US010640478B2

(12) United States Patent
Ochoa Gómez et al.

(10) Patent No.: US 10,640,478 B2
(45) Date of Patent: May 5, 2020

(54) GLYCIDOL SYNTHESIS METHOD

(71) Applicant: FUNDACION TECNALIA RESEARCH & INNOVATION, Derio (ES)

(72) Inventors: José Ramón Ochoa Gómez, Miñano (ES); Olga Gómez De Miranda Jiménez De Aberastui, Miñano (ES); Noelia Blanco Pérez, Miñano (ES); Belén Maestro Madurga, Miñano (ES); Soraya Prieto Fernández, Miñano (ES)

(73) Assignee: FUNDACION TECNALIA RESEARCH & INNOVATION, Derio (ES)

( * ) Notice: Subject to any disclaimer, the term of this patent is extended or adjusted under 35 U.S.C. 154(b) by 0 days.

(21) Appl. No.: 15/748,599

(22) PCT Filed: Jul. 28, 2016

(86) PCT No.: PCT/ES2016/070573
§ 371 (c)(1),
(2) Date: Jan. 29, 2018

(87) PCT Pub. No.: WO2017/017307
PCT Pub. Date: Feb. 2, 2017

(65) Prior Publication Data
US 2018/0319756 A1 Nov. 8, 2018

(30) Foreign Application Priority Data

Jul. 30, 2015 (ES) .................. 201531136

(51) Int. Cl.
| | | |
|---|---|---|
| *C07D 301/02* | (2006.01) | |
| *C07D 303/14* | (2006.01) | |
| *B01J 23/02* | (2006.01) | |
| *B01J 23/20* | (2006.01) | |
| *B01J 23/04* | (2006.01) | |
| *B01J 37/02* | (2006.01) | |
| *B01J 37/04* | (2006.01) | |
| *B01J 21/04* | (2006.01) | |
| *B01J 21/06* | (2006.01) | |
| *B01J 21/08* | (2006.01) | |
| *B01J 21/10* | (2006.01) | |
| *B01J 23/10* | (2006.01) | |
| *B01J 23/14* | (2006.01) | |

(52) U.S. Cl.
CPC ............ *C07D 303/14* (2013.01); *B01J 21/04* (2013.01); *B01J 21/066* (2013.01); *B01J 21/08* (2013.01); *B01J 21/10* (2013.01); *B01J 23/02* (2013.01); *B01J 23/04* (2013.01); *B01J 23/10* (2013.01); *B01J 23/14* (2013.01); *B01J 23/20* (2013.01); *B01J 37/0201* (2013.01); *B01J 37/04* (2013.01); *C07D 301/02* (2013.01)

(58) Field of Classification Search
CPC ....... C07D 303/14; C07D 301/02; B01J 23/14; B01J 23/10; B01J 23/02; B01J 23/20; B01J 21/04; B01J 21/066; B01J 21/10; B01J 21/08
USPC .......................................... 549/518
See application file for complete search history.

(56) References Cited

U.S. PATENT DOCUMENTS

| 2,856,413 A | 10/1958 | Malkenus et al. |
| 5,164,497 A * | 11/1992 | King ............ B01J 21/02 544/177 |
| 5,359,094 A | 10/1994 | Teles et al. |
| 6,316,641 B1 | 11/2001 | Yoo et al. |
| 7,868,192 B1 | 1/2011 | Seki et al. |
| 7,888,517 B2 | 2/2011 | Uno et al. |
| 2014/0135512 A1 | 5/2014 | Lee et al. |

FOREIGN PATENT DOCUMENTS

CN 103554060 A 2/2014

OTHER PUBLICATIONS

International Search Report dated Nov. 3, 2016 for PCT/ES2016/070573, 17 pages, with English translation.
Algoufi, Y.T., et al: "One-pot synthesis of glycidol from glycerol and dimethyl carbonate over KF/sepiolite catalyst", Applied Catalysis A: General, Sep. 17, 2014, vol. 487, pp. 181-188.
Bai, R., et al: "One-pot synthesis of glycidol from glycerol and dimethyl carbonate over a highly efficient and easily available solid catalyst NaAlO2", Green Chemistry, Aug. 1, 2013, vol. 15, pp. 2929-2934.
Bolívar-Díaz, C.L., et al: "New concepts for process intensification in the conversion of glycerol carbonate to glycidol", Applied Catalysis B: Environmental 2013, Oct. 18, 2012, vol. 129, pp. 575-579.
Choi, J.S., et al: "Ionic-liquid-catalyzed decarboxylation of glycerol carbonate to glycidol", Journal of Catalysis 2013, Nov. 17, 2012, vol. 297, pp. 248-255.
Ertl, G., et al: "Handbook in Heterogeneous Catalysis", 2nd edition, vol. 2, Wiley-VCH, 2008.
Fujita, Shin-ichiro, et al: "Synthesis of glycerol carbonate from glycerol and urea using zinc-containing solid catalysts: A homogeneous reaction", Journal of Catalysis, Nov. 5, 2012, vol. 297, pp. 137-141.

(Continued)

Primary Examiner — Taylor V Oh
(74) Attorney, Agent, or Firm — Squire Patton Boggs (US) LLP

(57) ABSTRACT

The invention relates to a method for obtaining glycidol in a semi-continuous or continuous manner by decarboxylating glycerol carbonate at reduced pressure, at a temperature less than or equal to 130° C. and in the presence of alkoxide catalysts of alkaline metals and alkaline earth metals, metal oxides, mixed metal oxides, metal stannates and mixed metal stannates, all of which optionally supported via $SiO_2$, $\gamma$-$Al_2O_3$, MgO and $ZrO_2$.

18 Claims, No Drawings

(56) References Cited

OTHER PUBLICATIONS

Gade, S. M., et al: "Synthesis of glycidol from glycerol and dimethyl carbonate using ionic liquid as a catalyst", Catalysis Communications, Jul. 3, 2012, vol. 27, pp. 184-188.
Kleemann, Axel, et al: "Glycidol: Properties, reactions, applications", 1981, Heidelberg; Basel; Nueva York: A. Hüthig; ISBN: 3-7785-0709-5.
Munshi, M.K., et al: "Role of cation-anion cooperation in the selective synthesis of glycidol from glycerol using DABCO-DMC ionic liquid as catalyst", Jul. 14, 2014, Royal Society of Chemistry Advances 2014, vol. 4, pp. 32127-32133.
Ochoa-Gómez, Jose R., et al: "Synthesis of glycerol carbonate from glicerol and dimethyl carbonate by transesterification: Catalyst screening and reaction optimization", Applied Catalysis A: General, Jul. 23, 2009, vol. 366, pp. 315-324.
Zhou, Yan, et al, et al: "Facile one-pot synthesis of glycidol from glycerol and dimethyl carbonate catalyzed by tetraethylammonium amino acid ionic liquids", Catalysis Communications, Mar. 13, 2015, vol. 66, pp. 25-29.
Du, Meimei, et al., "Synthesis of glycerol carbonate from glycerol and dimethyl carbonate catalyzed by K2CO3/MgO", Research on Chemical Intermediates, Mar. 2012, vol. 38, Issue 3-5, pp. 1069-1077.

\* cited by examiner

GLYCIDOL SYNTHESIS METHOD

The present invention relates to a method for obtaining glycidol by catalytic decarboxylation of 4-hydroxymethyl-1,3-dioxolan-2-one (referred to as glycerin carbonate in this specification) at temperatures equal to or less than 130° C. using as catalysts alkoxides of alkaline metals and alkaline earth metals, metal oxides, mixed metal oxides, metal stannates and mixed metal stannates, all of which without support or supported via $SiO_2$, $\gamma$-$Al_2O_3$, MgO and $ZrO_2$ and operating at reduced pressure.

BACKGROUND OF THE INVENTION

An exhaustive description of the methods for obtaining glycidol may be found in Axel Kleemann & Rudolf M. Wagner (1981). *Glycidol: Properties, reactions, applications*. Heidelberg; Basel; New York: A. Hüthig; ISBN: 3-7785-0709-5. Glycidol can thus be obtained by epoxidation of allylic alcohol with hydrogen peroxide, hyperperoxides or percarboxylic acids; by dehydrohalogenation of monohalohydrins of glycerol using hydroxides of alkaline metals or alkaline earth metals; from acrolein by epoxidation and subsequent catalytic hydrogenation of the glycidaldehyde obtained using sodium chromate in tetrahydrofuran or metallic hydride reducing agents such as potassium borohydride in ethanol-water or lithium hydride and aluminum in absolute ether.

All these processes have the common drawback of using highly toxic raw materials. In addition, the epoxidation of allylic alcohol, carried out industrially by Degussa AG (at present Evonik Industries) using hydrogen peroxide and a catalyst based on $NaHWO_4$ is an industrially inconvenient process, since on the one hand, in the reaction step a reaction system is used formed by three reactors connected in series plus a fourth to ensure the consumption of the hydrogen peroxide traces, and on the other hand in the separation step, an evaporator and five distillation columns are used since the reaction mixture is formed by allylic alcohol without reaction, glycidol, the catalyst, water and small amounts of impurities such as glycerol, acrolein, beta-hydroxypropionaldehyde, glycerin-1-allyl ether and beta-allyloxypropionaldehyde. The dehydrohalogenation of monohalohydrins of glycerol, since it is not a catalytic process, uses stoichiometric or greater quantities of hydroxides of alkaline metals or alkaline earth metals causing the generation of enormous quantities of the corresponding halides therefore it is not economically profitable if said halides are not used in an adjacent production plant for electrolytically regenerating the hydroxides, a process which consumes a large quantity of energy. The epoxidation of the acrolein followed by the hydrogenation of the intermediate glycidaldehyde has the drawback that low outputs are obtained if sodium chromite is used as the catalyst or that very expensive reducing agents are used such as metal hydrides which negate the industrial viability of the process.

Given the drawbacks of said methods, alternative methods have been sought for producing glycidol, such as the method which proceeds using glycerol carbonate, a non-toxic compound which can be easily produced from glycerol by reacting both with urea (S. Fujita, Y. Yamanishi, M. Arai, *ournal of Catalysis* 2013, 297, 137-141) and with dimethyl carbonate (J. R. Ochoa-Gómez, O-Jiménez-Aberasturi, B. Maestro-Madurga, A. Pesquera-Rodríguez, C. Ramírez-López, L. Lorenzo-lbarreta, J. Torrecilla-Soria, M. C. Villarán-Velasco. Applied Catalysis: *General A* 2009, 366, 315-324).

Obtaining glycidol by decarboxylating glycerol carbonate can be carried out thermally in a vacuum (to continuously separate glycidol and avoid its polimerization) without the use of a catalyst as emerges in examples 4 and 5 (not part of the invention) of this specification and is described in the U.S. Pat. No. 7,888,517 B2. The method is especially advantageous with respect to the other methods for obtaining glycidol described above, since pure glycidol is obtained in only one step by combining the decarboxylation of the glycerol carbonate with the separation by evaporation in a vacuum of the glycidol formed. However, obtaining industrially significant outputs, for example of 60% or more requires work at high temperatures, greater than 175° C. At temperatures of 140-160° C., the outputs do not exceed 45%, reducing in accordance with the reduction of the temperature, such that at 140° C. they are less than 2% and there is no reaction at temperatures equal to or less than 130° C. (see the examples 1-5 (not part of the invention) of this specification).

Therefore, the methods that have been available up to now for obtaining glycidol from glycerol carbonate are carried out in a vacuum and at temperatures greater than 150° C., more frequently at temperatures greater than 175° C. which involves high power consumption. Thus, for example, document U.S. Pat. No. 7,888,517 B2 describes a method for obtaining glycidol from glycerol carbonate in a vacuum without using a catalyst or using as such a neutral salt of an alkaline metal such as sodium sulfate or chloride or an alkaline earth metal. Such a method leads to low outputs of 39-45% when it is carried out at temperatures between 155° C. and 160° C. (examples 2 to 4 of said invention) and requires continuous work at a temperature of 200° C. (drop by drop addition of glycerol carbonate) to obtain high outputs (66% to 79%, examples 4 and 5 of said invention). It is therefore a method that is very expensive in terms of energy costs.

Document U.S. Pat. No. 2,856,413 describes a method for obtaining glycidol from glycerol carbonate using such basic catalysts as phosphates, pyrophosphates, chlorides, bromides, acetates, carbonates and bicarbonates of alkaline metals and alkaline earth metals. As patented in the examples, the obtainment of outputs greater than 72% requires work in a vacuum and at temperatures greater than 195° C. Therefore this method is also very expensive in terms of energy costs.

Document U.S. Pat. No. 5,359,094 describes a method for obtaining glycerol carbonate by carboxylation of glycerol. The synthesis of glycidol is not claimed, however, in its specification (page 2, lines 25-40) its synthesis by decarboxylation of glycerol carbonate is mentioned using a most preferred temperature range of 210 to 275° C., as is exemplified in its examples 3 and 4 and using as catalysts salts of alkaline metals or alkaline earth metals, such as halides, phosphates, monohydrogen phosphates, pyrophosphates, sulfates, borates, acetates, carbonates and bicarbonates. The method is very expensive in terms of energy costs.

Document U.S. Pat. No. 6,316,641 describes a method for obtaining glycidol from organic cyclic carbonates, in particular glycerol carbonate, in a vacuum in the presence of a polyol as a solvent and a solid catalyst which comprises a type A zeolite or $\gamma$-alumina. However, temperatures greater than 165° C. are claimed, temperatures greater than 180° C. being necessary for obtaining outputs greater than 70%, therefore this method is also very expensive in terms of energy costs. In addition, the active hydrogens of the terminal hydroxy groups of the polyol may be activated, producing the ring-opening polymerization both of the starting glycerol carbonate and the formed glycidol.

Document U.S. Pat. No. 7,868,192 B1 describes a method for obtaining glycidol from glycerol carbonate in a vacuum in the presence of solvents which do not have active hydrogens such as liquid parafins and/or polyalkylene glycol dimethyl ether, using neutral salts of alkaline metals and alkaline earth metals as catalysts. There is no temperature range claimed but the one used in the examples is between 180° C. (output 60%, in a vacuum, example 5) and 250° C. (example 6: environmental pressure, nitrogen bubbling, output 70%). This method is also very expensive in terms of energy costs.

Document US 2014/0135512 A1 describes a method for obtaining glycidol from glycerol carbonate using as catalysts ionic liquids derived from methyl imidazolium in which the anion of the ionic liquids has a basicity in the range of 0.60 to 0.80 based on the Kamlet-Taft parameter. The ionic liquids can be used alone or in combination with a Lewis acid metallic salt such as $Zn(NO_3)_2$, $ZnCl_2$, $SnCl_4$, $MgCl_2$, $AlCL_3$ and its mixtures. This method has the drawbacks of high cost of the ionic liquids and the high working temperature between 165° C. and 175° C. for obtaining outputs of industrial interest such as emerge in Table 6 of said document. The output of the reaction is 0% at 140° C.

In addition, various methods have been described for obtaining glycidol at temperatures lower than 100° C., proceeding from glycerol and dimethyl carbonate, using superbase catalysts such as DBU and ionic liquids and quaternary ammonium hydroxide. The glycerol reacts with the dimethyl carbonate in the presence of the basic catalyst to give glycerol carbonate which decarboxylates to glycidol. See for example, S. K. Gade, M. K. Munshi, B. M. Chherawalla, V. H. Rane, A. A. Kelkar, *Catal. Commun.* 2012, 27 184-88; R. Bai, H. Zhang, F. Mei, S. Wang, T. Li, Y. Gu, G. Li, *Green Chem.* 2013, 15, 2929-2934; Y. T. Algoufi, U. G. Akpan, M. Asif, B. H. Hameed, *Appl. Catal. A Gen.* 2014, 487, 181-188, M. K. Munshi, S. M. Gade, V. H. Rane, A. A. Kelkar, *RSC Adv.* 2014, 4, 32127-32133 and Y. Zhou, F. Ouyang, Z.-B. Song, Z. Yang and D.-J. Tao, *Catal. Commun.* 2015, 66, 25-29. However, these methods lead to a complex mixture formed by the reagents without reacting, intermediate glycerol carbonate without reacting, glycidol as well as the catalysts and solvents used from which it is difficult to separate the glycidol given the ease with which it polymerizes. These methods are therefore not industrially viable.

Therefore, there is a need for an industrially viable method for producing glycidol.

DESCRIPTION OF THE INVENTION

The inventors propose an industrially viable method for producing glycidol from glycerol carbonate which drastically reduces the energy consumption of the existing methods. This method has been achieved by means of the novel use of catalysts that are described below, which permit a working temperature less than or equal to 130° C.

Thus, the present invention relates to a method for producing glycidol by decarboxylation of glycerol carbonate which comprises the steps:

a) Placing into contact, optionally in the presence of an organic solvent, glycerol carbonate with a catalyst selected from the group consisting of ($C_1$-$C_n$) alkoxides of alkaline metals and alkaline earth metals, metal oxides, mixed metal oxides, metal stannates, mixed metal stannates and mixtures thereof, wherein the catalyst is optionally supported via a support selected from the group consisting of $SiO_2$, $\gamma$-$Al_2O_3$, MgO and $ZrO_2$; and b) Carrying out the reaction at a temperature less than or equal to 130° C. at reduced pressure to continuously separate the glycidol formed by evaporation.

The optional solvent should have a boiling point such that it does not separate from the reaction medium by evaporation at the reduced working pressure and preferably does not have active hydrogens, that is to say hydrogens which can react with basic sites producing the formation of alkoxides which can initiate the ring-opening polymerization both of the starting glycerol carbonate and the glycidol formed with the consequent drastic reduction of the glycidol output. Non-limiting examples of solvents are polyethers with their protected OH terminal groups, for example forming ethers, such as for example polyethylene glycol 400, 600 or 2000 dimethyl ether or tetra methylene glycol dimethyl ether.

The reaction can be carried out both in a semi-continuous and continuous manner. In the first manner, the glycerol carbonate and the catalyst are introduced in the reactor and the glycidol is separated continuously by evaporation at reduced pressure. In the second method, the glycerol carbonate is continuously fed at a predetermined flowrate to the reactor in which the catalyst has been previously introduced and the glycidol is continuously separated by evaporation at reduced pressure.

In a particular embodiment, the catalysts are ($C_1$-$C_n$) alkoxides of alkaline metals and alkaline earth metals and are preferably selected from the group consisting of sodium methoxide, potassium methoxide, sodium ethoxide and potassium ethoxide. The term "($C_1$-$C_n$) alkoxide" refers to the radical —O($C_1$-$C_n$) alkyl wherein the term alkyl refers to a saturated, linear or branched hydrocarbon chain which contains 1 to n atoms of carbon. The alkoxide group is saturated and contains only single bonds. The saturated "($C_1$-$C_n$) alkoxide" can be substituted or unsubstituted as described in this description.

In another particular embodiment, the metal oxide catalysts are selected from the group consisting of oxides of alkaline metal and alkaline earth metals and metals selected from zirconium, niobium, scandium, yttrium, lanthanum, zinc, cerium and tin which can be used without support or supported via $SiO_2$, $\gamma$-$Al_2O_3$, MgO and $ZrO_2$, that is to say, optionally supported via $SiO_2$, $\gamma$-$Al_2O_3$, MgO and $ZrO_2$.

In another particular embodiment, the catalysts are mixed metal oxides and are selected from the group consisting of mixtures of two or more alkaline metal oxides and alkaline earth metals and metals selected from zirconium, niobium, scandium, yttrium, lanthanum, zinc, cerium and tin which can be used without support or supported via $SiO_2$, $\gamma$-$Al_2O_3$, MgO and $ZrO_2$.

In another particular embodiment, the catalysts are metal stannates and mixed metal stannates and are selected from the group consisting of metal stannates and mixed metal stannates of alkaline metals and alkaline earth metals, preferably of sodium and potassium. These catalysts are optionally supported via $SiO_2$, $\gamma$-$Al_2O_3$, MgO and $ZrO_2$. The metal stannate catalysts are obtained by calcination of the corresponding commercial stannates hydrated at temperatures greater than 200° C. The mixed metal stannate catalysts are obtained both by mechanically mixing the corresponding hydrated commercial stannates and calcinating at temperatures greater than 200° C. or dissolving the corresponding commercial stannates hydrated in water, evaporating the water, drying the residue and calcinating at temperatures greater than 200° C. The metal stannate and supported mixed metal stannate catalysts can, for example, be obtained by impregnating the support with an aqueous solution of the metal stannates to be deposited, drying the mixture and calcinating. The term "stannate" includes orthostannates and metastannates. Therefore, the invention relates to metal orthostannates and metastannates and to mixed metal orthostannates and metastannates.

The catalysts formed by oxides and mixed oxides, supported or unsupported, can be produced by means of any of the methods known in the art. Thus, for example, they can be obtained by means of: mechanical mixing, wet impregnating of the oxide which acts as a support with solutions of precursor agents of the oxide to be deposited (non-limiting examples are nitrates, sulfates, chlorides, acetates, formates and oxalates of the corresponding metals) followed by drying and calcination; co-precipitation in basic medium of metal hydroxides from aqueous solutions of salts which contain the corresponding metals (non-limiting examples are nitrates, sulfates, chlorides, acetates, formates and oxalates of the corresponding metals) followed by drying and calcination; precipitation in basic medium of metal hydroxides over one of the oxides from aqueous solutions of salts which contain the corresponding metals (non-limiting examples are nitrates, sulfates, chlorides, acetates, formates and oxalates of the corresponding metals) followed by drying and calcination; and sol-gel methods. A large number of references concerning these and other reference methods can be found in the bibliography. See for example Handbook in Heterogeneous Catalysis, Ed. Ertl, Knözinger, Schüth, Weitkamp, 2nd edition, vol 2, Wiley-VCH, 2008.

The concentration of catalyst, in percentage by weight with respect to the glycerol carbonate, can vary between 0.001% and 10%, but preferably is comprised between 0.001% and 1%, because higher concentrations in many cases lead to a reduction of the output. Without wishing to be bound in any way by theory, it is believed that the cause is due to the fact that high concentrations of catalyst drastically increase the ring-opening polymerization both of the starting glycerol carbonate and the glycidol formed, producing the formation of polyglycerols with the consequent reduction of the glycidol output.

The working temperature is less than or equal to 130° C. and in one particular embodiment is preferably between 100° C. and 130° C.

In one particular embodiment of the invention, the working pressure is less than or equal to 2 kPa, preferably less than or equal to 1 kPa and most preferably is comprised between 0.2 kPa and 1 kPa. When "reduced pressure" is mentioned in the present invention, it is understood as any pressure below atmospheric pressure.

The reaction time will depend both on the time it takes to completely convert the glycerol carbonate and the type of catalyst, the working pressure and the temperature. The reaction times according to the present invention are comprised between 30 mins and 7 hours, preferably 1 hour and 4 hours.

The invention is illustrated by means of the following examples which are provided exclusively in an illustrative manner and which do not intend to in any way limit the scope of the invention.

EXAMPLES

General Synthetic Method

All the reactions were carried out at reduced pressure in a 100 ml glass reactor, connected to a vacuum pump. The reactor was submerged in a bath placed on top of a heating plate to regulate the reaction temperature. A condenser was placed between the reactor and the pump, through whose liner a cooling liquid circulated at −10° C., connected to a collection container of the glycidol submerged in a cooling bath at −10° C. In a semi-continuous mode of operation, 0.065 moles of glycerol carbonate and the quantity of catalyst specified in each example were introduced into the reactor. The reaction was maintained with magnetic stirring at the reduced temperature and pressure selected during the reaction time desired to continuously separate by evaporation the glycidol formed. When the reaction finished, the vacuum was stopped and the glycidol accumulated in the condenser was weighed to calculate the output.

In the continuous mode of operation, the experimental system was the same with the exception that the glycerol carbonate was fed continuously to the reactor with a HPLC pump at a predetermined flowrate.

In the present specification, all the concentrations of catalyst are in % by weight relative to the quantity of glycerol carbonate.

Examples 1 to 5

Not Part of the Invention

Various experiments were carried out according to the semi-continuous mode of operation previously described, without catalyst and at different temperatures between 130 and 175° C. The results are given in Table 1. The examples 1 and 2 reveal that there is no reaction below 130° C., example 3 demonstrates that the reaction at 140° C. is virtually non-existent and examples 4 and 5 reveal that temperatures as high as 170° C. are necessary for obtaining outputs of industrial interest.

TABLE 1

| Example | T(° C.) | Pressure (kPa) | Time (h) | Y (%) |
|---------|---------|----------------|----------|-------|
| 1 | 125 | 0.25 | 3 | 0 |
| 2 | 130 | 0.65 | 3 | 0 |
| 3 | 140 | 0.65 | 6 | 2 |
| 4 | 170 | 0.65 | 3 | 59 |
| 5 | 175 | 0.65 | 3 | 58 |

* Y: glycidol output

Example 6

Of the Invention

A reaction was carried out according to the semi-continuous mode of operation previously described using as a catalyst $Cs_2O$ supported via $\gamma$-$Al_2O_3$ with a content of $Cs_2O$ of 60% by weight, prepared by the method of wet impregnation and calcinated at 900° C. The concentration of catalyst was 0.65%, the reaction time 6 hours, the pressure 0.25 kPa and the temperature 120° C. The glycidol output was 65.5%.

This example and those below reveal how the use of one of the catalysts of the invention allows the reaction to be carried out at a temperature of 120° C., much lower than that of the known methods used at present for obtaining glycidol by decarboxylation of glycidol carbonate with an output which means that the process is industrially viable.

Example 7

Of the Invention

A reaction like in example 6 was carried out but with a concentration of catalyst of 0.60%, a reaction time of 5 hours and a temperature of 125° C. The glycidol output was 68.4%.

Example 8

Of the Invention

A reaction according to a semi-continuous mode of operation was carried out using as a catalyst $Cs_2O$ supported via MgO with a content of $Cs_2O$ of 30% by weight, prepared by the method of wet impregnation and calcinated at 600° C. The concentration of catalyst was 0.2%, the reaction time 6.5 hours, the pressure 0.25 kPa and the temperature 130° C. The glycidol output was 70.5%.

Example 9

Of the Invention

A reaction according to a semi-continuous mode of operation was carried out using as a catalyst $Cs_2O$ supported via MgO with a content of $Cs_2O$ of 30% by weight, prepared by the method of wet impregnation and calcinated at 600° C. The concentration of catalyst was 0.27%, the reaction time 4.5 hours, the pressure 0.25 kPa and the temperature 130° C. The glycidol output was 70.4%.

Example 10

Of the Invention

A reaction according to a semi-continuous mode of operation was carried out using as a catalyst $Cs_2O$ obtained by calcinating cesium carbonate at 600° C. The concentration of catalyst was 0.2%, the reaction time 3 hours, the pressure 0.25 kPa and the temperature 130° C. The glycidol output was 67%.

Example 11

Of the Invention

A reaction according to a semi-continuous mode of operation was carried out using as a catalyst CaO calcinated at 900° C. The concentration of catalyst was 0.16%, the reaction time 6 hours, the pressure 0.25 kPa and the temperature 130° C. The glycidol output was 67%.

Example 12

Of the Invention

A reaction according to a semi-continuous mode of operation was carried out using as a catalyst $Cs_2O$ supported via $ZrO_2$ with a content of CaO of 5% by weight, prepared by the method of wet impregnation and calcinated at 800° C. The concentration of catalyst was 0.5%, the reaction time 6 hours, the pressure 0.25 kPa and the temperature 130° C. The glycidol output was 53.4%.

Example 13

Of the Invention

A reaction according to a semi-continuous mode of operation was carried out using as a catalyst $Na_2SnO_3$ obtained by calcinating the trihydrate at 350° C. The concentration of catalyst was 0.09%, the reaction time 6 hours, the pressure 0.25 kPa and the temperature 125° C. The glycidol output was 66%.

Example 14

Of the Invention

A reaction according to a semi-continuous mode of operation was carried out using as a catalyst $Na_2SnO_3$ supported via γ-$Al_2O_3$ with a content of $Na_2SnO_3$ of 60% by weight, prepared by the method of wet impregnation and calcinated at 600° C. The concentration of catalyst was 0.47%, the reaction time 5 hours, the pressure 0.25 kPa and the temperature 125° C. The glycidol output was 69%.

Example 15

Of the Invention

A reaction according to a semi-continuous mode of operation was carried out using as a catalyst $K_2O$ supported via MgO with a content of $K_2O$ of 30% by weight, prepared by the method of wet impregnation from KOH and calcinated at 600° C. The concentration of catalyst was 0.2%, the reaction time 6.5 hours, the pressure 0.25 kPa and the temperature 125° C. The glycidol output was 66%.

Example 16

Of the Invention

A reaction according to a semi-continuous mode of operation was carried out using as a catalyst $K_2O$ supported via MgO with a content of $K_2O$ of 30% by weight, prepared by the method of wet impregnation from KOH and calcinated at 700° C. The concentration of catalyst was 0.43%, the reaction time 7 hours, the pressure 0.25 kPa and the temperature 125° C. and polyethylene glycol dimethyl ether was used with a molecular weight of 2000 in a proportion of 55.5% by weight with respect to the total of solvent and glycerol carbonate. The glycidol output was 74%.

Example 17

Of the Invention

A reaction according to a semi-continuous mode of operation was carried out using as a catalyst MgO calcinated at 600° C. The concentration of catalyst was 0.46%, the reaction time 6 hours, the pressure 0.25 kPa and the temperature 130° C. The glycidol output was 56%.

Example 18

Of the Invention

A reaction according to a semi-continuous mode of operation was carried out using as a catalyst sodium methoxide. The concentration of catalyst was 0.45%, the reaction time 2 hours, the pressure 0.20 kPa and the temperature 125° C. The glycidol output was 60.7%.

Example 19

Of the Invention

A reaction according to a semi-continuous mode of operation was carried out using as a catalyst a mechanically prepared mixture of $Na_2SnO_3$ and $Sc_2O_3$, with a content of $Sc_2O_3$ of 37% by weight and calcinated at 350° C. The concentration of catalyst was 1.5%, the reaction time 2 hours, the pressure 0.25 kPa and the temperature 125° C. The glycidol output was 59%.

The invention claimed is:

1. A method for producing glycidol by decarboxylating glycerol carbonate, which comprises the steps:
   a) Placing into contact glycerol carbonate with a catalyst selected from the group consisting of ($C_1$-$C_2$) alkoxides metal oxides, mixed metal oxides, metal stannates, mixed metal stannates and mixtures thereof; and
   b) Carrying out the reaction at a temperature less than or equal to 130° C. at reduced pressure to continuously separate the glycidol formed by evaporation, wherein the ($C_1$-$C_2$) alkoxides, metal oxides, mixed metal oxides, metal stannates, and mixed metal stannates are of alkaline metals or alkaline earth metals.

2. The method according to claim 1, wherein the catalysts are selected from the group consisting of sodium methoxide, potassium methoxide, sodium ethoxide and potassium ethoxide.

3. The method according to claim 1, wherein the metal stannates and mixed metal stannates of alkaline metals are from sodium and potassium.

4. The method according to claim 1, wherein the concentration of catalyst is comprised between 0.001% and 10%, in percentage by weight with respect to the glycerol carbonate.

5. The method according to claim 1, wherein the concentration of catalyst is comprised between 0.001% and 1%, in percentage by weight with respect to the glycerol carbonate.

6. The method according to claim 1, wherein the working pressure is less than or equal to 2 kPa.

7. The method according to claim 1, wherein the working pressure is less than or equal to 1 kPa.

8. The method according to claim 1, wherein the working pressure is comprised between 0.2 kPa and 1 kPa.

9. The method according to claim 1, wherein the temperature of the reaction is in the range of 100 to 130° C.

10. The method according to claim 1, which is carried out in a semi-continuous manner.

11. The method according to claim 1, which is carried out in a continuous manner.

12. The method according to claim 1, wherein the catalysts are metal oxides selected from the group consisting of oxides of alkaline metals and alkaline earth metals; wherein the concentration of catalyst is comprised between 0.001% and 1%, in percentage by weight with respect to the glycerol carbonate.

13. The method according to claim 1, wherein the catalysts are metal oxides selected from the group consisting of oxides of alkaline metals and alkaline earth metals; wherein the concentration of catalyst is comprised between 0.001% and 1%, in percentage by weight with respect to the glycerol carbonate; and wherein the working pressure is less than or equal to 1 kPa.

14. The method according to claim 1, wherein the catalysts are metal oxides selected from the group consisting of oxides of alkaline metals and alkaline earth metals; wherein the concentration of catalyst is comprised between 0.001% and 1%, in percentage by weight with respect to the glycerol carbonate; wherein the working pressure is less than or equal to 1 kPa; and wherein the temperature of the reaction is in the range of 100 to 130° C.

15. The method according to claim 1, wherein the catalysts are metal oxides selected from the group consisting of oxides of alkaline metals and alkaline earth metals; wherein the concentration of catalyst is comprised between 0.001% and 1%, in percentage by weight with respect to the glycerol carbonate; wherein the working pressure is less than or equal to 1 kPa; wherein the temperature of the reaction is in the range of 100 to 130° C.; and which is carried out in a semi-continuous manner.

16. The method according to claim 1, wherein the catalysts are stannates and are selected from the group consisting of metal stannates and mixed metal stannates of alkaline metals and alkaline earth metals; wherein the metal stannates and mixed metal stannates of alkaline metals are from sodium and potassium; and wherein the concentration of catalyst is comprised between 0.001% and 1%, in percentage by weight with respect to the glycerol carbonate.

17. The method according to claim 1, wherein the catalysts are stannates and are selected from the group consisting of metal stannates and mixed metal stannates of alkaline metals and alkaline earth metals; wherein the metal stannates and mixed metal stannates of alkaline metals are from sodium and potassium; wherein the concentration of catalyst is comprised between 0.001% and 1%, in percentage by weight with respect to the glycerol carbonate; wherein the working pressure is less than or equal to 1 kPa; wherein the temperature of the reaction is in the range of 100 to 130° C.; and which is carried out in a semi-continuous manner.

18. The method according to claim 1, wherein the catalyst is supported via a support selected from the group consisting of $SiO_2$, $\gamma$-$Al_2O_3$, MgO, and $ZrO_2$.

* * * * *